(12) United States Patent
Quadling et al.

(10) Patent No.: US 7,142,312 B2
(45) Date of Patent: Nov. 28, 2006

(54) LASER DIGITIZER SYSTEM FOR DENTAL APPLICATIONS

(75) Inventors: Henley Quadling, Addison, TX (US); Mark Quadling, Plano, TX (US); Alan Blair, St. Paul, MN (US)

(73) Assignee: D4D Technologies, LLC, Richardson, TX (US)

( * ) Notice: Subject to any disclaimer, the term of this patent is extended or adjusted under 35 U.S.C. 154(b) by 363 days.

(21) Appl. No.: 10/749,579

(22) Filed: Dec. 30, 2003

(65) Prior Publication Data

US 2004/0201856 A1  Oct. 14, 2004

Related U.S. Application Data

(60) Provisional application No. 60/437,373, filed on Dec. 31, 2002.

(51) Int. Cl.
  *G01B 11/24* (2006.01)
  *G01B 11/30* (2006.01)
  *G06K 9/00* (2006.01)
  *A61C 5/00* (2006.01)

(52) U.S. Cl. .................. 356/602; 356/603; 356/608; 382/154; 433/215

(58) Field of Classification Search ............... None
  See application file for complete search history.

(56) References Cited

U.S. PATENT DOCUMENTS

| | | | |
|---|---|---|---|
| 4,411,626 A | 10/1983 | Becker et al. |
| 4,478,580 A | 10/1984 | Barrut |
| 4,575,805 A | 3/1986 | Moermann et al. |
| 4,611,288 A | 9/1986 | Duret et al. |
| 4,615,678 A | 10/1986 | Moermann et al. |
| 4,663,720 A | 5/1987 | Duret et al. |
| 4,742,464 A | 5/1988 | Duret et al. |
| 4,752,964 A | 6/1988 | Okada et al. |
| 4,766,704 A | 8/1988 | Brandestini et al. |
| 4,798,534 A | 1/1989 | Breads |
| 4,816,920 A | 3/1989 | Paulsen |
| 4,856,991 A | 8/1989 | Breads et al. |
| 4,935,635 A | 6/1990 | O'Harra |
| 4,936,862 A | 6/1990 | Walker et al. |
| 4,952,149 A | 8/1990 | Duret et al. |
| 4,964,770 A | 10/1990 | Steinbichler et al. |
| 4,970,032 A | 11/1990 | Rotsaert |
| 5,027,281 A | 6/1991 | Rekow et al. |
| 5,035,613 A | 7/1991 | Breads et al. |
| 5,055,039 A | 10/1991 | Abbatte et al. |
| 5,059,118 A | 10/1991 | Breads et al. |

(Continued)

FOREIGN PATENT DOCUMENTS

EP  0 600 800 A1  6/1994

OTHER PUBLICATIONS

Baumgartner, A., "Polarization-Sensitive Optical Coherence Tomography of Dental Structures", *Caries Res.*, vol. 34, 2000, pp. 59-69.

(Continued)

*Primary Examiner*—Hwa (Andrew) Lee
*Assistant Examiner*—Gordon J. Stock, Jr.
(74) *Attorney, Agent, or Firm*—David H. Judson

(57) ABSTRACT

A laser digitizer system provides a visual three-dimensional image of a real-world object such as a dental item through a laser digitization. The laser digitizer captures an image of the object by scanning multiple portions of the object in an exposure period.

18 Claims, 6 Drawing Sheets

U.S. PATENT DOCUMENTS

| | | | |
|---|---|---|---|
| 5,092,022 A | | 3/1992 | Duret |
| 5,106,303 A | | 4/1992 | Oden et al. |
| 5,139,419 A | | 8/1992 | Andreiko et al. |
| 5,151,044 A | | 9/1992 | Rotsaert |
| 5,168,386 A | * | 12/1992 | Galbraith ............... 359/215 |
| 5,186,623 A | | 2/1993 | Breads et al. |
| 5,224,049 A | | 6/1993 | Mushabac |
| 5,257,184 A | | 10/1993 | Mushabac |
| 5,266,030 A | | 11/1993 | Van Der Zel |
| 5,273,429 A | | 12/1993 | Rekow et al. |
| 5,280,542 A | * | 1/1994 | Ozeki et al. ............ 382/154 |
| 5,338,198 A | | 8/1994 | Wu et al. |
| 5,340,309 A | | 8/1994 | Robertson |
| 5,342,202 A | | 8/1994 | Deshayes |
| 5,342,696 A | | 8/1994 | Eidenbenz et al. |
| 5,347,454 A | | 9/1994 | Mushabac |
| 5,368,478 A | | 11/1994 | Andreiko et al. |
| 5,372,502 A | | 12/1994 | Massen et al. |
| 5,378,154 A | | 1/1995 | Van Der Zel |
| 5,382,164 A | | 1/1995 | Stern |
| 5,383,752 A | | 1/1995 | Rheinberger et al. |
| 5,386,292 A | | 1/1995 | Massen et al. |
| 5,395,238 A | | 3/1995 | Andreiko et al. |
| 5,417,572 A | | 5/1995 | Kawai et al. |
| 5,431,562 A | | 7/1995 | Andreiko et al. |
| 5,440,393 A | | 8/1995 | Wenz |
| 5,440,496 A | | 8/1995 | Andersson et al. |
| 5,447,432 A | | 9/1995 | Andreiko et al. |
| 5,448,472 A | | 9/1995 | Mushabac |
| 5,452,219 A | | 9/1995 | Dehoff et al. |
| 5,454,717 A | | 10/1995 | Andreiko et al. |
| 5,474,448 A | | 12/1995 | Andreiko et al. |
| RE35,169 E | | 3/1996 | Lemchen et al. |
| 5,497,336 A | | 3/1996 | Andersson et al. |
| 5,533,895 A | | 7/1996 | Andreiko et al. |
| 5,545,039 A | | 8/1996 | Mushabac |
| 5,549,476 A | | 8/1996 | Stern |
| 5,562,448 A | | 10/1996 | Mushabac |
| 5,569,578 A | | 10/1996 | Mushabac |
| 5,587,912 A | | 12/1996 | Andersson et al. |
| 5,604,817 A | * | 2/1997 | Massen et al. ............ 382/120 |
| 5,607,305 A | | 3/1997 | Andersson et al. |
| 5,652,709 A | | 7/1997 | Andersson et al. |
| 5,683,243 A | | 11/1997 | Andreiko et al. |
| 5,691,905 A | | 11/1997 | Dehoff et al. |
| 5,725,376 A | | 3/1998 | Poirier |
| RE35,816 E | | 6/1998 | Schulz |
| 5,788,498 A | | 8/1998 | Wohlwend |
| 5,800,174 A | | 9/1998 | Andersson |
| 5,812,269 A | | 9/1998 | Svetkoff et al. |
| 5,813,859 A | | 9/1998 | Hajjar et al. |
| 5,818,587 A | | 10/1998 | Devaraj et al. |
| 5,823,778 A | | 10/1998 | Schmitt et al. |
| 5,832,107 A | * | 11/1998 | Choate ............... 382/154 |
| 5,851,115 A | | 12/1998 | Carlsson et al. |
| 5,857,853 A | | 1/1999 | van Nifterick et al. |
| 5,870,220 A | | 2/1999 | Migdal et al. |
| 5,879,158 A | | 3/1999 | Doyle et al. |
| 5,880,962 A | | 3/1999 | Andersson et al. |
| 5,882,192 A | | 3/1999 | Bergersen |
| 5,938,446 A | | 8/1999 | Andersson et al. |
| 5,975,893 A | | 11/1999 | Chishti et al. |
| 6,015,289 A | | 1/2000 | Andreiko et al. |
| 6,044,170 A | | 3/2000 | Migdal et al. |
| 6,049,743 A | | 4/2000 | Baba |
| 6,062,861 A | | 5/2000 | Andersson |
| 6,068,482 A | | 5/2000 | Snow |
| 6,099,314 A | | 8/2000 | Kopelman et al. |
| 6,115,114 A | | 9/2000 | Berg et al. |
| 6,135,774 A | | 10/2000 | Hack et al. |
| 6,152,731 A | | 11/2000 | Jordan et al. |
| 6,200,135 B1 | | 3/2001 | Hultgren |
| 6,205,240 B1 | | 3/2001 | Pietrzak et al. |
| 6,206,693 B1 | | 3/2001 | Hultgren |
| 6,210,162 B1 | | 4/2001 | Chishti et al. |
| 6,217,325 B1 | | 4/2001 | Chishti et al. |
| 6,227,850 B1 | | 5/2001 | Chishti et al. |
| 6,227,851 B1 | | 5/2001 | Chishti et al. |
| 6,244,861 B1 | | 6/2001 | Andreiko et al. |
| 6,250,918 B1 | | 6/2001 | Sachdeva et al. |
| 6,287,119 B1 | | 9/2001 | van Nifterick et al. |
| 6,287,121 B1 | | 9/2001 | Guiot et al. |
| 6,315,553 B1 | | 11/2001 | Sachdeva et al. |
| 6,318,995 B1 | | 11/2001 | Sachdeva et al. |
| 6,322,359 B1 | | 11/2001 | Jordan et al. |
| 6,334,773 B1 | | 1/2002 | Ahlen et al. |
| 6,350,120 B1 | | 2/2002 | Sachdeva et al. |
| 6,359,680 B1 | | 3/2002 | Rubbert |
| 6,364,660 B1 | | 4/2002 | Durbin et al. |
| 6,382,975 B1 | | 5/2002 | Poirier |
| 6,386,867 B1 | | 5/2002 | Durbin et al. |
| 6,386,878 B1 | | 5/2002 | Pavlovskaia et al. |
| 6,394,801 B1 | | 5/2002 | Chishti et al. |
| 6,398,548 B1 | | 6/2002 | Muhammad et al. |
| 6,398,554 B1 | | 6/2002 | Perot et al. |
| 6,402,707 B1 | | 6/2002 | Ernst |
| 6,406,292 B1 | | 6/2002 | Chishti et al. |
| 6,409,504 B1 | | 6/2002 | Jones et al. |
| 6,413,084 B1 | | 7/2002 | Rubbert et al. |
| 6,431,870 B1 | | 8/2002 | Sachdeva |
| 6,457,972 B1 | | 10/2002 | Chishti et al. |
| 6,463,344 B1 | | 10/2002 | Pavloskaia et al. |
| 6,464,496 B1 | | 10/2002 | Sachdeva et al. |
| 6,471,512 B1 | | 10/2002 | Sachdeva et al. |
| 6,482,284 B1 | | 11/2002 | Reidt et al. |
| 6,497,574 B1 | | 12/2002 | Miller |
| 6,499,997 B1 | | 12/2002 | Chishti et al. |
| 6,506,054 B1 | | 1/2003 | Shoher et al. |
| 6,512,994 B1 | | 1/2003 | Sachdeva |
| 6,514,074 B1 | | 2/2003 | Chishti et al. |
| 6,532,299 B1 | | 3/2003 | Sachdeva et al. |
| 6,540,512 B1 | | 4/2003 | Sachdeva et al. |
| 6,554,611 B1 | | 4/2003 | Chishti et al. |
| 6,554,613 B1 | | 4/2003 | Sachdeva et al. |
| 6,568,936 B1 | | 5/2003 | MacDougald et al. |
| 2002/0143506 A1 | | 10/2002 | D'Aligny et al. |
| 2003/0045798 A1 | | 3/2003 | Hular et al. |

OTHER PUBLICATIONS

Otis, Lind et al., "Identification of Occlusal Sealants Using Optical Coherence Tomography", *J. Clin. Den.*, vol. XIV, No. 1, 2003, pp. 7-10.

Otis, Linda et al., "Optical Coherence Tomography: A New Imaging Technology for Dentistry", *JADA*, vol. 131, 2000, pp. 511-514.

International Search Report for corresponding PCT application No. PCT/US03/41701, dated Jun. 4, 2004, 4 pages.

* cited by examiner

Top View

Front View

LASER DIGITIZER SYSTEM FOR DENTAL APPLICATIONS

PRIORITY AND CROSS REFERENCE TO RELATED APPLICATION

This application claims the benefit under 35 U.S.C. § 119(e) of co-pending provisional application Ser. No. 60/437,373 filed Dec. 31, 2002, which is incorporated in its entirety herein by reference.

BACKGROUND OF THE INVENTION

1. Related Field

The invention relates to three-dimensional imaging of physical objects. In particular, the invention relates to laser imaging of dental items including molds, castings, dentition, prepared dentition and the like.

2. Description of the Related Art

Techniques have been developed to generate three-dimensional ("3D") visual images of physical objects. The 3D image may be generated by a computer that processes data representing the surfaces and contours of a physical object. The computer displays the 3D image on a screen or a computer monitor. The data may be generated by optically scanning the physical object and detecting or capturing the light reflected off of the object. Based on processing techniques such as Moiré, interferometry, and laser triangulation the shape, surfaces and/or contours of the object may be modeled by the computer.

The Moiré technique uses a structured white light to project a 2D image on the object to be imaged. The Moiré technique uses a pattern that has a sinusoidal intensity pattern. The projected image intensity pattern observed from a position other than the projected angle does not appear sinusoidal. Therefore, an inferred point-by-point phase angle between an observed and a projected image may be correlated to the height data Z at each observed pixel point. Interferometry methods may then use a reference beam and a scanning beam to infer 3D information based on an optical interference between the two beams.

Laser triangulation methods project a laser dot or beam onto an object from a known direction. The laser beam is scanned across the surface of the object following an arc. The laser beam is imaged by an imaging system from a different known direction. The known baseline and angle between the projector and imaging system provides sufficient information to deduce the 3D location of the reflected dot from the surface of the object being scanned, utilizing known triangulation techniques. Such scanning may also result in an inaccurate reading of depth of field and uniformity of a line width due to the scanned arc. Systems have been developed using special optics that increase the depth measurement and resolution. However, some special optics adversely effect and distort the optical image and limit the speed at which the system may acquire sufficient data to generate a 3D image.

Laser triangulation methods also may scan one or more laser lines across an object. The laser lines may be generated through a diffractive lens. However, the intensity of the laser line(s) may vary along the length of the projected line(s), resulting in inaccurate measurements and imaging of the object. The laser line systems are also susceptible to laser speckle, which may appear as a mottled pattern of randomly distributed "blobs of light." Laser speckle may be caused by an interference at the image plane of coherent light reflected by a rough surface. The mottled pattern may introduce noise and uncertainty into the measurement, due to a difficulty in distinguishing between useful intensity data, and speckle intensity data.

Current laser systems used in dental applications may be rudimentary and limited by the projection of a single laser line. Such systems are not adjustable for a desired line pattern and lack any correction or minimization of a non-flat or non-linear scanning field or correction for laser speckle. Also, such systems may have a limited clamping and holding mechanism which limit the range of molds or castings for which the digitizer may be used.

BRIEF SUMMARY OF THE INVENTION

The embodiments provide a laser imaging system that generates a three-dimensional image of a scanned physical object such as a dental item. An embodiment includes laser imaging systems, methods, apparatuses, and techniques that provide laser digitization of a physical object to obtain a visual image of the object. The visual image may be displayed on a computer monitor, screen, display, or the like.

A laser digitizer may include a light source, a scanner, a flat-field lens, an image capture instrument, and a processor configured to carry out instructions based on code, and process digital data. The laser digitizer may also include an object positioning system for positioning an object within a field of view of the scanner and the image capture instrument.

The light source may include a laser LED and collimating optics configured to produce a collimated beam of light. The collimated beam of light is projected to the scanner. The scanner redirects or scans the collimated beam of light so that the beam is scanned through at least two axes. The scanned beam is projected toward the lens, which focuses the beam as a dot on the surface of the object. As the scanner scans the beam in a desired pattern, the lens focuses the dot on the object so that the dot traverses a curvilinear segment across the object. The image capture instrument detects the light reflected from the object and generates data representing a captured image of the scanned beam. The image capture system may be configured to capture images of one or more scanned curvilinear segments during an exposure period. The computer processes the data to generate the three-dimensional visual image of the object on a computer monitor, a screen, or other display. Multiple images of the object may be recorded and processed by the computer to produce a three-dimensional map of the object. The multiple images can be captured from multiple positions and orientations of the object. The individual images are merged to create an overall three-dimensional ("3D") map of the object.

Other systems, methods, features and advantages of the invention will be, or will become, apparent to one with skill in the art upon examination of the following figures and detailed description. It is intended that all such additional systems, methods, features and advantages be included within this description, be within the scope of the invention, and be protected by the following claims.

BRIEF DESCRIPTION OF THE DRAWINGS

The invention can be better understood with reference to the following drawings and description. The components in the figures are not necessarily to scale, emphasis instead being placed upon illustrating the principles of the invention. Moreover, in the figures, like referenced numerals designate corresponding parts throughout the different views.

DESCRIPTION OF THE EMBODIMENTS OF THE INVENTION

Figure 1:
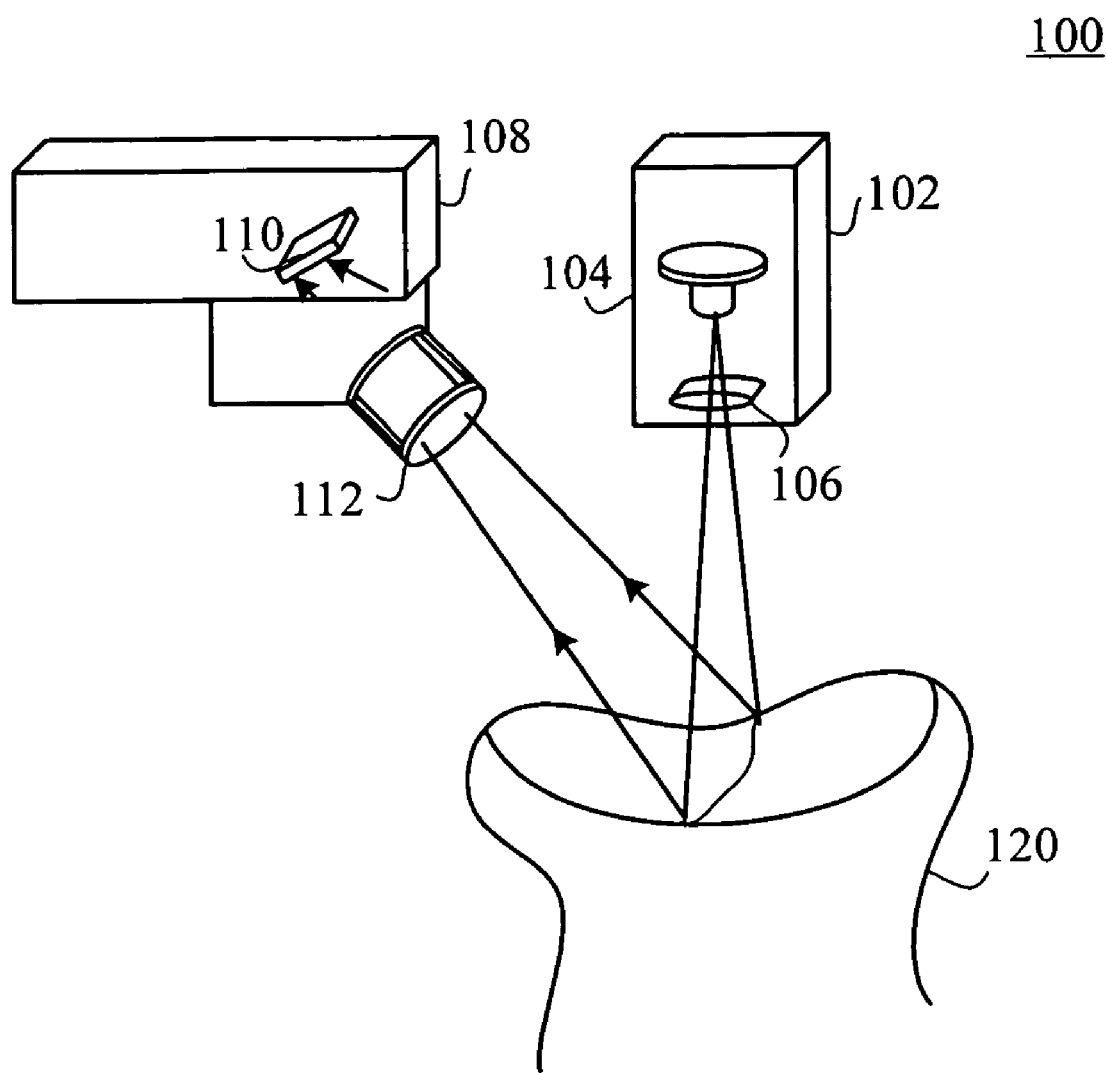
FIG. 1 illustrates an example of a prior art laser line system.

FIG. 1 illustrates an example of a prior art laser line imaging system 100. The prior art laser line imaging system 100 has a transmitter 102 and a receiver 108. The transmitter 102 includes a laser light source 104 and transmission optics 106. The transmitter 102 projects a planar laser light on an object 120 within a field of view of the transmitter 102. The planar laser light incident on the object forms a straight line on the object 120. The projected laser line is produced by either a cylindrical lens or diffractive optical element 106.

The light reflected from the object 120 is detected by the camera 108. The camera 108 has an optical axis at a known angle to the transmitter 102. The light is picked up by an optical lens 112 which focuses the reflected light onto a matrix of photo-detectors 110. The contour of the object 120 having differences in the elevation can be imaged based on the image projected on the matrix of photo-detectors 110.

Figure 2A:
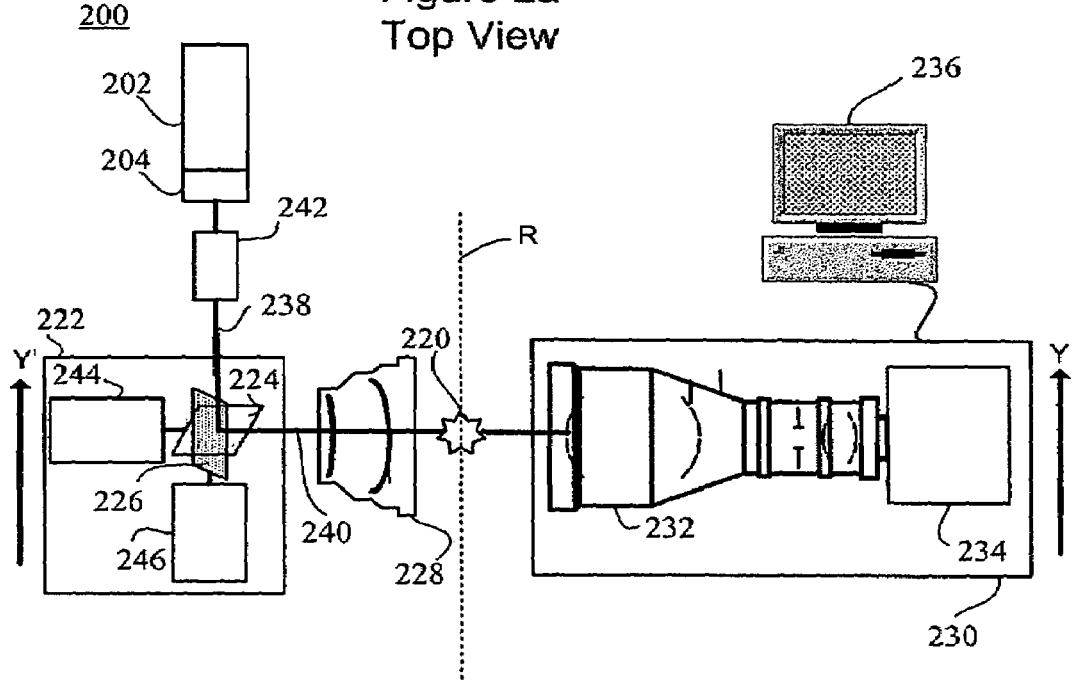
FIG. 2a illustrates a top view of a laser digitizer system for dental applications.
Figure 2B:
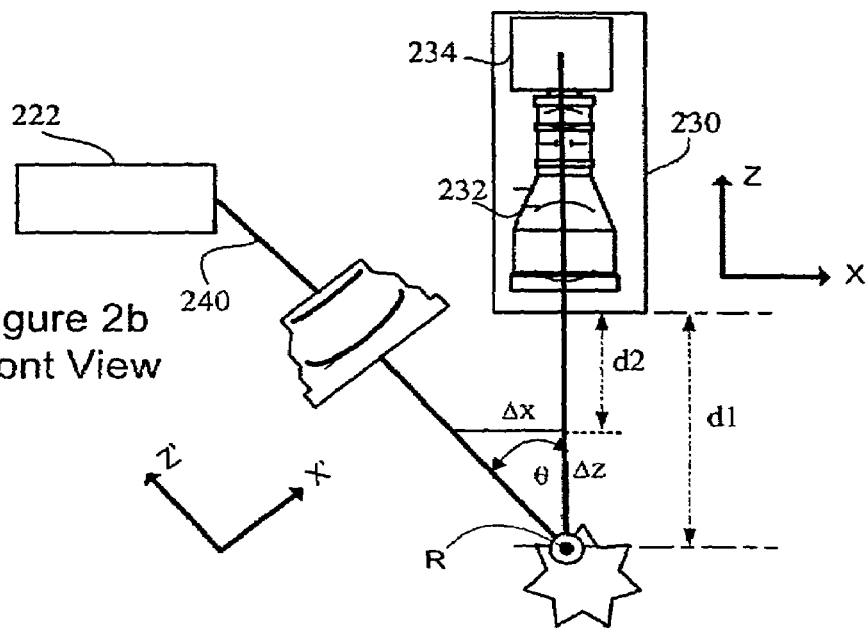
FIG. 2b illustrates a front view of a laser digitizer system for dental applications.

FIGS. 2a and 2b illustrate an example of a laser digitizer system 200 configured to generate a 3D image of a dental item. The laser digitizer system 200 includes a laser light source 202, an optical scanner 222, a flat-field lens 228, that may be known as an F-Theta lens, an image capture instrument 230, and a processor 236. The laser digitizer system 200 may also include a positioner (not shown) for securing and positioning an object to be imaged. The laser digitizer system 200 may also include a variable beam expander 242 optically positioned between the laser source and the scanner 222.

The laser light source 202 generates a laser beam that is projected and scanned across an object to be imaged by the scanner 222 and the F-Theta lens 228. The scanned light is reflected from the object 220 and detected by the image capture instrument 230, which generates a signal representative of the detected light.

The laser light source 202 may include collimating optics 204 that produce a collimated light beam 238 having parallel rays of laser light. This collimated light beam 238 is projected towards a two-axis optical scanner 222.

The laser light source 202 may include a laser diode or LED configured to generate a laser light beam that may have an elliptical-shaped beam. The collimating optics may be configured to circularize the elliptical beam and to generate a circular spot. The circular spot may be used to scan a uniform line across the surface of the object 220. The laser diode may be any commercially available laser diode configured to emit a laser light beam, such as a 10 mW laser diode from Blue Sky Research having a 4 mm beam size at a 635 nm wavelength (part number MINI-0635-101C40W).

The laser light source 202 also may be configured to modulate laser light. The laser light source 202 also may be coupled to a modulator that adjusts or interrupts light flow from the source at high modulation or switching rate such as 20 MHz rate. By switching the laser light source 202, the coherence of the laser light emitted from the laser light source 202 may be reduced, thereby reducing speckle.

The scanner 222 redirects or scans the collimated light beam 238 to form a scanned light beam 240 having a position that may vary over time. The scanned beam 240 is directed by the scanner 222 to the F-theta lens 228. The scanner 222 redirects the collimated light beam across two axes where each axis is substantially perpendicular to the axis of the collimated light beam 238. The scanned light beam 240 may be scanned in at least two or more axes.

The scanner 222 includes a first reflector 224 and a second reflector 226. The first and second reflectors 224, 226 may comprise optical mirrors or surfaces capable of reflecting undiffused light to form an image. Each reflector 224, 226 may be rotatably coupled with a respective motor 244, 246. Each motor 244, 246 may comprise a galvo drive motor, or the like, that controls a rotational movement of the respective reflector 244, 226 to effect the scanning of the collimated light beam 238.

The first and second reflectors 224, 226 may have essentially perpendicular axes, and may be essentially orthogonal with respect to each other. The reflectors 224, 226 also may be positioned at an arbitrary angle relative to each other. Additional reflectors may also be included. The reflectors 224, 226 may be positioned orthogonally so that the collimated laser beam 238 incident on the reflectors may be scanned or redirected in at least two axes. The first reflector 224 scans the beam along one axis, such as an x-axis. The second reflector 226 may be positioned so that the beam along the x-axis incident upon the second reflector 226 may be scanned along an orthogonal direction to the x-axis, such as a y-axis. For example, the first and second reflectors 224, 226 may be positioned orthogonal with respect to each other so that the first reflector scans the beam along the x-axis and the second reflector 226 scans the beam along an orthogonal direction to the x-axis, such as a y-axis.

The first reflector 224 also may comprise a spinning polygon mirror such that the rotatable second reflector 226 and the spinning polygon reflector 224 together also are configured to scan the laser beam in two axes. The spinning polygon mirror 224 may scan the collimated light beam 238 along an x-axis and the rotatable mirror 226 may scan the collimated light beam along a y-axis. Each axis, the x-axis and y-axis, may be substantially orthogonal with one another, thereby generating a scanned light beam 240 from the collimated beam 238 where the scanned light beam 240 is scanned along two substantially orthogonal axes.

The scanner 222 also may include a programmable position controller. The position controller may be a component of the scanner 222 or may be incorporated with the processor 236. By incorporating the position controller with the scanner 222, computing resources of the processor 236 are available for other functions such as processing the image data or for more advanced processing. The position controller may comprise a commercially available controller such as the GSI Lumonics SC2000 Scanner Motion Controller which controls the scanning of the two reflectors. The controller may be configured to control the movement of the reflectors 224, 226 by controlling the motors 244, 246. The controller may control the movement of the reflectors 224, 226 so that the collimated laser beam 238 is redirected to provide to a desired scan sequence. A coordinate system for the scanner 222 is referred to as X'Y'Z'.

The scanned beam 240 is incident to the F-Theta lens 228. The F-theta lens 228 focuses the scanned beam 240 to a point or dot. The object 220 to be imaged is positioned within a field of view of F-Theta lens and the image capture instrument 230. The F-theta lens 228 has an optical axis at an angle θ with respect to an optical axis of the image capture instrument 230 so that when the focused dot is scanned across the surface of the object 220 the light is reflected towards the image capture instrument at angle θ. The scanner 222 moves the scanned beam 240 so that the focus point of the laser dot from the F-Theta leans 228 traverses through a pattern across the surface of the object 220. The F-Theta lens 228 may be any commercially available lens such as part number 4401-206-000-20 from Linos, having a 160 mm focal length, a 140 mm diagonal scanning length, +/−25 degree scanning angle and 633 nm working wavelength.

The image capture instrument 230 may be configured and/or positioned to have a field of view that includes the focused laser dot projected on the object 220. The image capture instrument 230 detects the laser dot as it is scanned across the surface of the object 220. The image capture instrument 230 may be sensitive to the light reflected from the object 220. Based on a light detected from the object 220, the image capture instrument generates an electrical signal representative of the surface characteristics (e.g., the contours, shape, arrangement, composition, etc.) of the object 220.

The image capture instrument 230 may include an imaging lens 232 and an image sensor 234. The imaging lens 232 is configured to focus the light reflected from the object 220 towards the image sensor 234. The imaging lens 232 may be a telecentric lens configured to minimize perspective errors. The imaging lens 232 may have an internal stop configured to image mostly parallel rays incident at a lens aperture to reduce or eliminate an effect of magnification and perspective correction. The imaging lens 232 may be any commercially available lens configured to minimize perspective distortions such that a lateral measurement on the image of an object does not depend on the distance of the object from the lens such as the China Daheng Corp. combination with front lens number GCO-2305 (50 mm diameter) and the back lens number GC0-2305 (8 mm diameter) where the back lens corresponds to the imaging capture instrument sensor size.

The image sensor 234 captures an image of the scanned surface of the object. The image sensor 234 may be a photo-sensitive or light sensitive device or electronic circuit capable of generating signal representative of intensity of a light detected. The image sensor 234 may include an array of photodetectors. The array of photodetectors may be a charge coupled device ("CCD") or a CMOS imaging device, or other array of light sensitive sensors capable of generating an electronic signal representative of a detected intensity of the light. The image sensor 234 may comprise a commercially available CCD or CMOS high resolution video camera having imaging optics, with exposure, gain and shutter control, such as Model SI-3170-CL from Silicon Imaging of Troy, N.Y. The image sensor 234 also may include a high bandwidth link to a framegrabber device, such as the PIXCI CL1 capture and control computer board from Epix, Inc.

Each photodetector of the array generates an electric signal based on an intensity of the light incident or detected by the photodetector. In particular, when light is incident to the photodetector, the photodetector generates an electrical signal corresponding to the intensity of the light. The array of photodetectors includes multiple photodetectors arranged so that each photodetector represents a picture element, or pixel of a captured image. Each pixel may have a discrete position within the array. The image capture instrument 230 may have a local coordinate system, XY such that each pixel of the scanned pattern corresponds to a unique coordinate (x,y). The array may be arranged according to columns and rows of pixels or any other known arrangement. By virtue of position of the pixel in the array, a position in the image plane may be determined. The image capturing instrument 230 thereby converts the intensity sensed by each pixel in the image plane into electric signals that represent the image intensity and distribution in an image plane.

The CMOS image sensor may be configured to have an array of light sensitive pixels. Each pixel minimizes any blooming effect such that a signal received by a pixel does not bleed into adjacent pixels when the intensity of the light is too high.

The scanner 222 may be configured to scan the laser beam 240 across the surface of the object 220 via the F-Theta lens 228 in many desired patterns. The pattern may be selected to cover a sufficient portion of the surface of the object 220 during a single exposure period. The pattern may also comprise one or more curves or any known pattern from which the characteristics, elevations and configurations of the surface of the object 220 may be obtained.

During an exposure period, an image of a portion of the surface of the object is captured. The beam 240 scan the object 220 via the scanner 222 and the F-Theta lens 228 in a selected pattern, allowing the imaging sensor 230 to detect the light reflected from object 220. The image sensor 230 generates data representative of the surface characteristics, contours, elevations and configurations of the scanned portion or captured image. The data representation may be stored in an internal or external device such as a memory.

During a subsequent scan period, the beam 240 is scanned in a pattern across an adjacent portion of the object 220 and an image of the adjacent portion is captured. The scanned beam 240 may scan a different area of the surface of the object 220 during subsequent exposure periods. After a several exposure periods in which the beam 240 is scanned across the various portions of the object 220 and images of those scanned portions captured, a substantial portion of the object may be captured.

The processor 236 is coupled to the image capture instrument 230 and configured to receive the signals generated by the image capture instrument 236 that represent images of the scanned pattern on the object 220.

The processor 236 also may be coupled to the laser light source and control selected or programmed applications of the laser light. The processor 236 also may be coupled with the scanner 222 and programmed to control the scanning of the collimated light 238.

Figure 3:
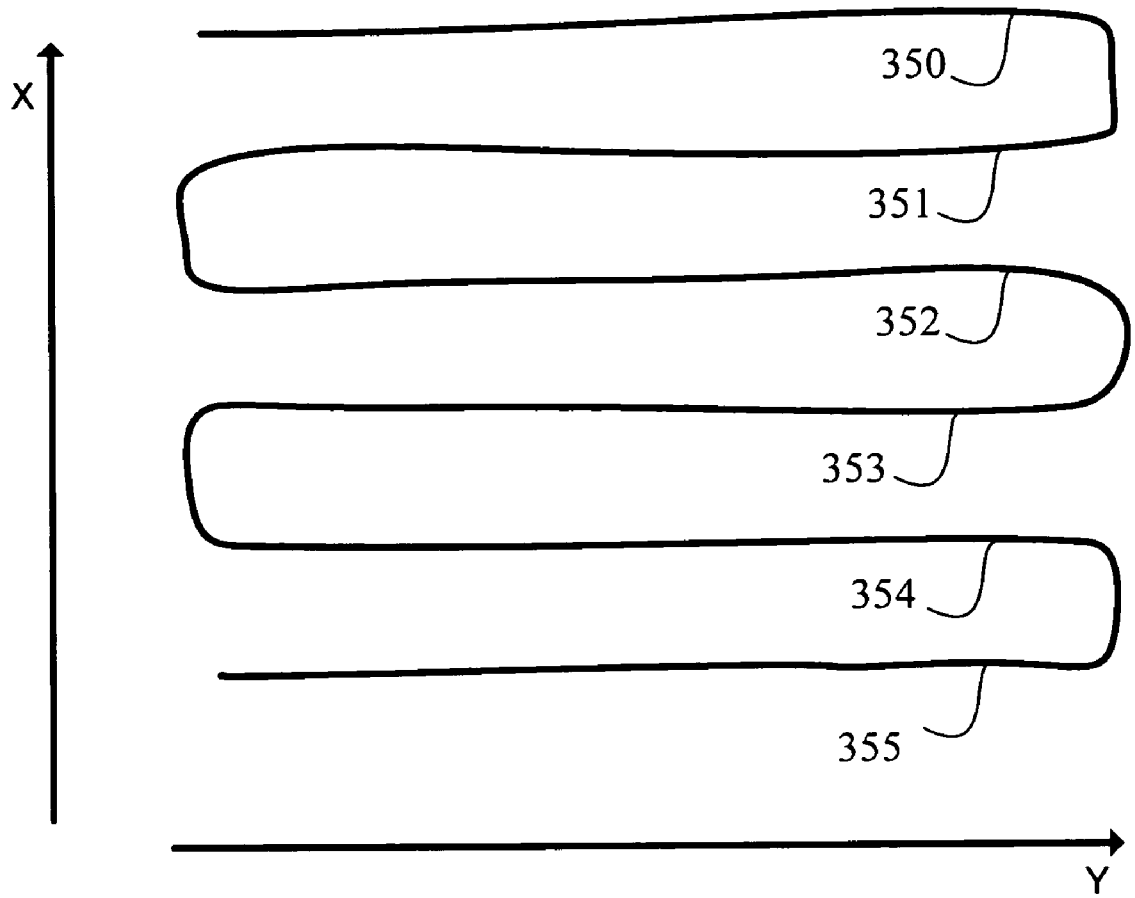
FIG. 3 illustrates an image of a light pattern of a laser digitizer of FIGS. 2a and 2b, as viewed on a flat surface.

FIG. 3 illustrates an example of a scanned pattern of light 348 as viewed from a substantially flat surface. The scanned pattern 348 may include multiple curves 350–355 that are generated by the scanner 222. A portion of the curves 350–351 may be essentially parallel to each other. The curves 350–355 also may represent or include a connected series of points or curvilinear segments where a tangent vector n at any single point or segment obeys the following rule:

$$|n \cdot R| \neq 0 \tag{1}$$

where R (as also seen in FIG. 2a) is a triangulation axis that is substantially parallel to Y and Y' and passes through an intersection of an axial ray from the image capture instrument 230 and an axial ray from the optical scanner 222. Accordingly, the angle between the tangent n at any point or segment of the curve and the triangulation axis R is not 90 degrees. Each curve 350–355 also may have a cross-sectional intensity characterized by a function that may have a sinusoidal variation, a Gaussian profile, or any other known function for cross-sectional intensity. In an embodiment, a minimum angle between a valid ray between the scanner 222 relative to a valid axial ray of the image sensor 234 is non-zero.

The image capture instrument 230 may be characterized by a local coordinate system XYZ, where the X and Y coordinates may be defined by the image capture instrument 230. A value for the Z coordinate may be based on the distance $d_1$ and $d_2$ so that $d_1 \leq z \leq d_2$. A point from a projected curve incident to a plane perpendicular to Z will appear to be displaced in the X direction by $\Delta x$. Based on a triangulation angle, the following condition may exist:

$$\Delta z = \frac{\Delta x}{\operatorname{Tan}\theta} \qquad (2)$$

For a given curve (e.g. curve 350) in the projection pattern there may be unique relations $\theta(y)$, $z_{base}(Y)$ and $x_{base}(Y)$. The relations $\theta(y)$, $z_{base}(Y)$ and $x_{base}(Y)$ relations may be determined through calibration. The calibration may be performed for example by observing the curve 350 as projected on a plane surface. The plane surface may be perpendicular to the image capture instrument 230 at two or more distances d along the Z axis from the image capture instrument 230. For each y value along the curve 350, using at least two such curves with known z values of $z_1$ and $z_2$, where $z_1 < z_2$, $\Delta z$ may be computed as $\Delta z = z_2 - z_1$. A value $\Delta x$ may be observed using the image capture instrument 230. Using equation (2), $\theta(y)$ may be computed. The corresponding value $z_{base}(y)$ may be set equal to $z_1$. The corresponding value $x_{base}(y)$ may be equal to an x value at the point y on the curve corresponding to $z_1$. Additional curves may be used to improve accuracy of through averaging or interpolation.

Figure 4:
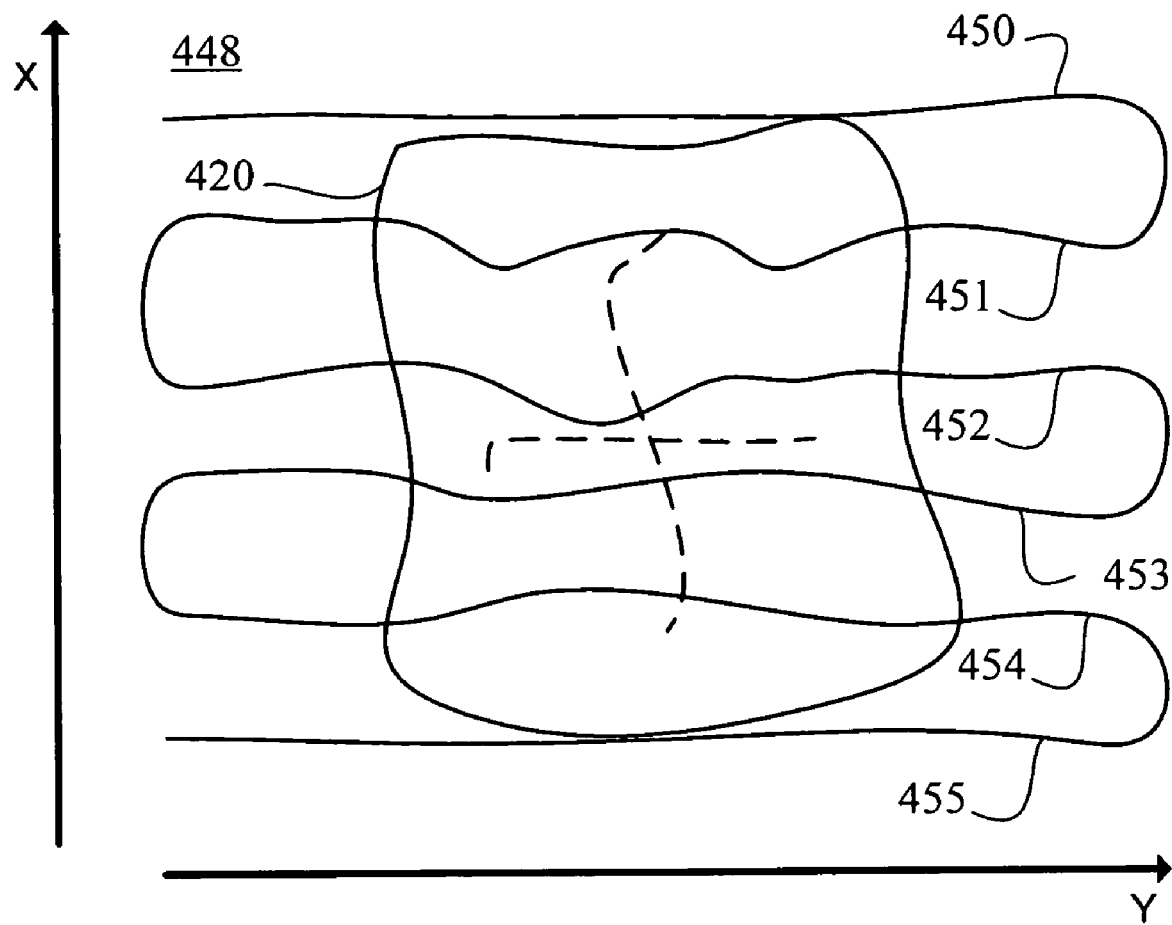
FIG. 4 illustrates the light pattern of FIG. 3 as projected on an object to be imaged.
Figure 5:
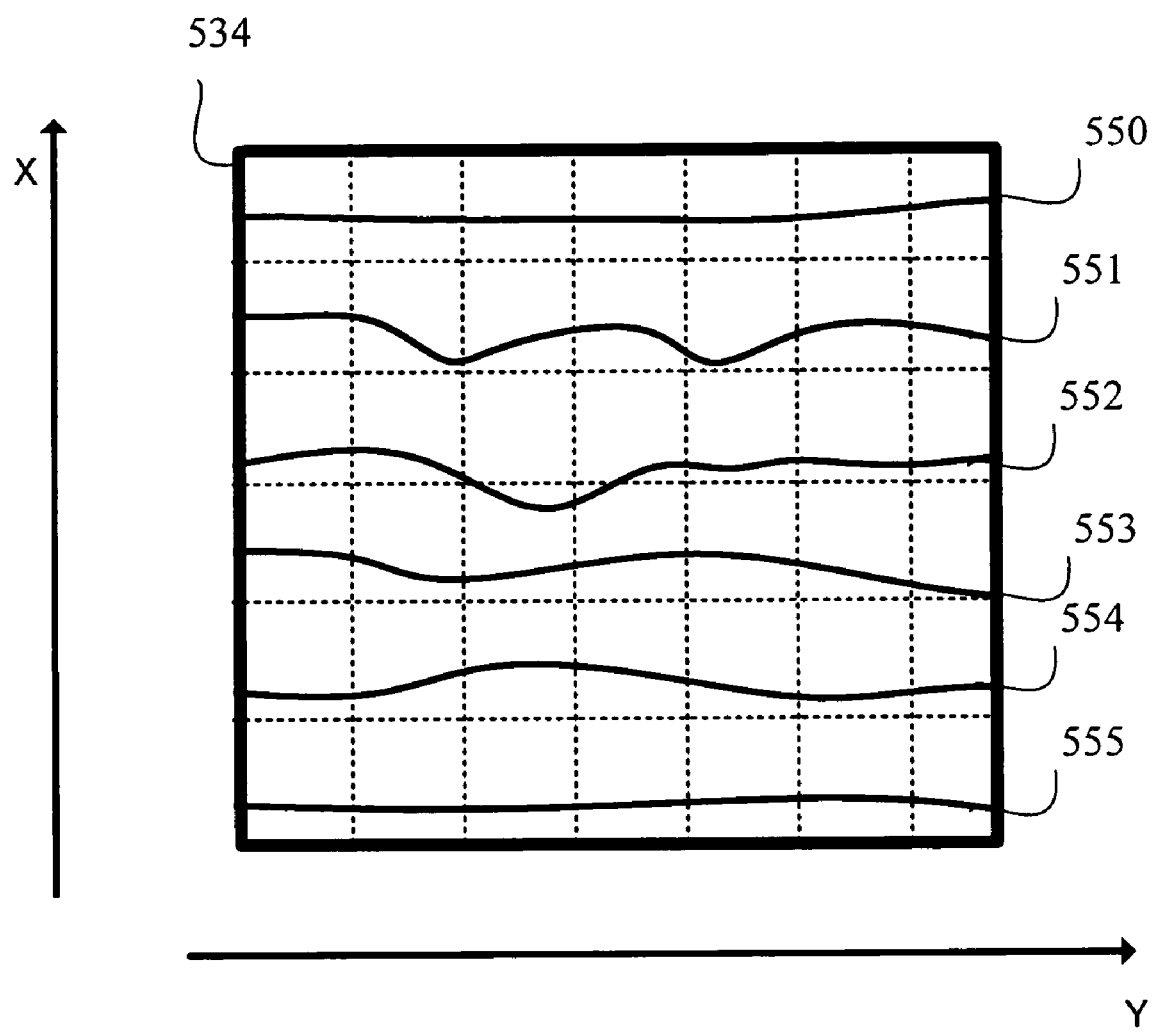
FIG. 5 illustrates a reflection of the light pattern of FIG. 3 as detected by image capture instrument.

FIG. 4 illustrates the scanned pattern of light 448 incident to the object 420 to be imaged. FIG. 5 illustrates the light pattern reflected from the object 420 as incident to the image sensor 534. For the observed projected curves 550–555 on the object, each curve corresponds to one of the curves 450–455 shown in FIG. 4 and a corresponding one of the curves 350–355 shown FIG. 3. Accordingly, for each curve 550–555, the corresponding relations $\theta(y)$, $z_{base}(y)$ and $x_{base}(y)$ may be selected that were precomputed during a calibration. For each point $(x_{observed}, y_{observed})$ on each curve 550–555, $$\Delta x = x_{observed} - x_{base}(y_{observed}) \qquad (3)$$

Equation (2) may be used to determine $\Delta z$ using $\theta(y_{observed})$, and consequently $$z_{observed} = \Delta z + z_{base}(y_{observed}) \qquad (4)$$

The collection of points $(x_{observed}, y_{observed}, z_{observed})$ obtained, form a 3D image of the object 420.

A maximum displacement for a curve may be determined by:

$$\Delta x = (d_1 - d_2)\operatorname{Tan}\theta \qquad (4)$$

A maximum number $n_{max}$ of simultaneously distinguishable curves 350 may be determined according to $n_{max} = X_{max}/\Delta x$ or equivalently $$n_{max} = \frac{X_{max}}{(d_1 - d_2)\operatorname{Tan}\theta_{max}} \qquad (4)$$

The number $n_{max}$ increases with a decreasing depth of field $d_1 - d_2$ and increases with a smaller $\theta_{max}$. The accuracy of the determination also may decrease with smaller $\theta_{max}$ values.

Figure 6:
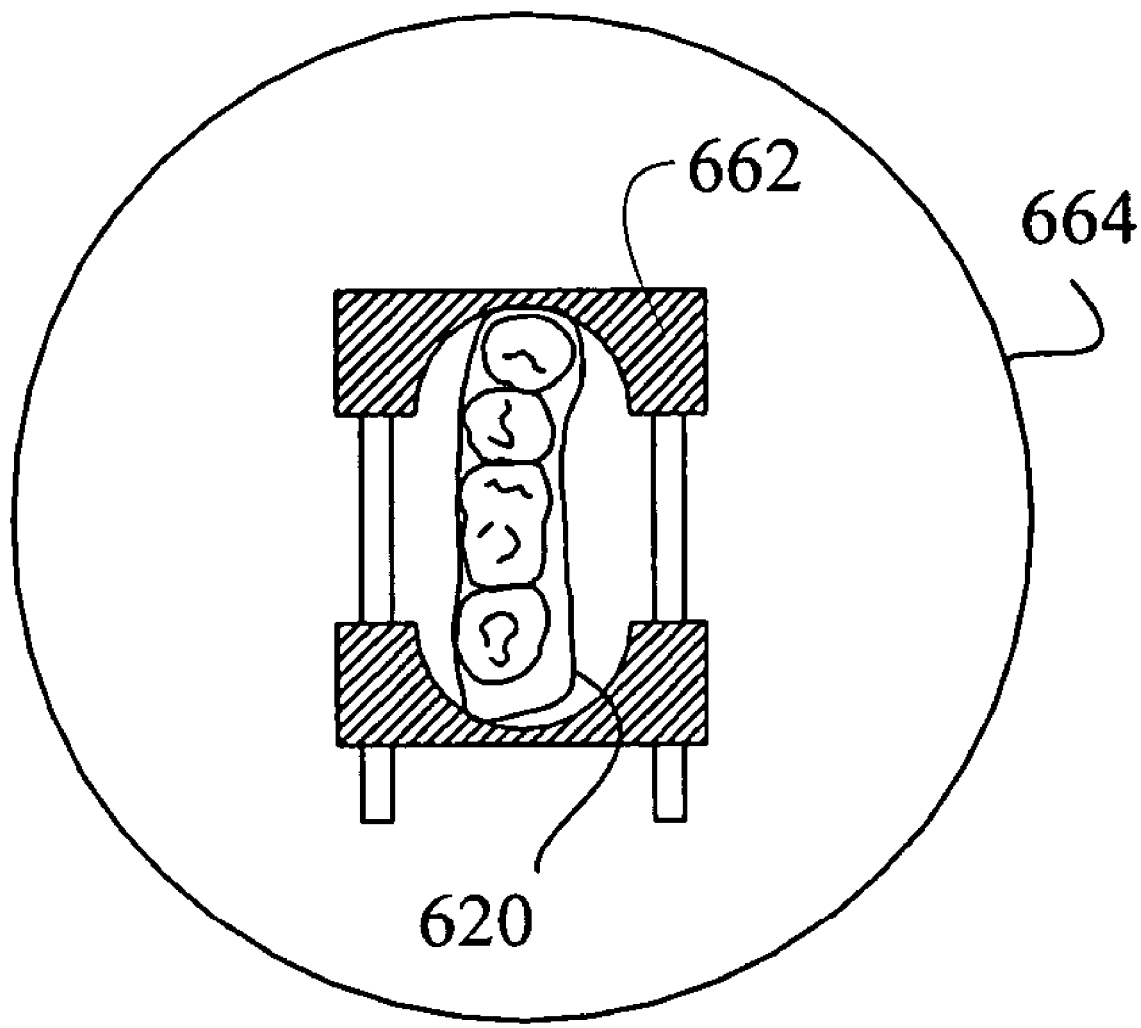
FIG. 6 illustrates an embodiment of an object positioner of the laser digitizer system of FIGS. 2a and 2b.

FIG. 6 illustrates an example of an object positioner 660. The positioner 660 is configured to secure and position an object 620 to be imaged in the field of view of the scanned laser beam 240 and the image capture instrument 230. The positioner 660 may include two or more rotary axes to provide for rotation of the object 620. The object 620 may be rotated with respect to the coordinate system XYZ of the image capture instrument 230. The positioner 660 also may include a linear axis to linearly adjust the object 620 to a focal point for the scanning system and image capture unit 230 system.

The positioner 660 also may include a platform 664 and a spring loaded clamp 662. The spring-loaded 662 clamp may be configured to securely hold a dental mold or dental casting 620. The clamp 662 also may have magnets (not shown) so that it may be rigidly secured through magnetic attraction to the positioning platform 664. This object 620 may be quickly positioned with the laser imaging system by securing it into the clamp 662 and placing the clamp onto the platform 664. The object 620 may be moved or adjusted with respect to the platform 664 to a desired the position appropriate for digitizing the region of interest.

Although embodiments of the invention are described in detail, it should be understood that various changes, substitutions and alterations can be made hereto without departing from the spirit and scope of the invention as described by the appended claims.

An example of the laser imaging system described above may include a three-dimensional imaging system having a light source and circularizing optics. The light or laser transmitted from the source may be modulated at high frequency for the purpose of reducing the coherence of the laser source and thus reducing the amount of speckle received by the imaging system. The system may include a variable beam expander, a multi-axis scanner system and a flat field scan lens. An image capture instrument may be focused to an area in which an object may be positioned by an adjustable positioner. The image capture system may include a telecentric imaging lens and CMOS imaging sensor. The adjustable positioner may secure dental items such as a dental mold, impressions, or castings. The dental item may be secured using a device such as a spring tensioned vise having magnets for securing the vise to a platform. The vise may be freely moved on and around the platform while holding the dental item solid in a desired position.

While various embodiments of the invention have been describe, it will be apparent to those of ordinary skill in the art that many more embodiments and implementations are possible within the scope of the invention. Accordingly, the invention is not to be restricted except in light of the attached claims and their equivalents.

What is claimed is:

1. A laser digitizer comprising:
a light source having collimating optics configured to generate a collimated beam of light;
a scanner optically coupled to the light source and configured to scan the collimated beam along at least two axes towards an object to be imaged to generate a pattern comprising a set of curvilinear segments;
an image capture instrument having an optical axis at an angle θ with respect to the scanner and configured to detect a reflection of the pattern from the object and to generate data representative of a surface of the object based on the reflection of the pattern; and
a processor coupled to the scanner and the image capture system configured to generate a three-dimensional image of the object based on the data.

2. The laser digitizer of claim 1 where the light source comprises a laser LED.

3. The laser digitizer of claim 1 further comprising a flat-field scan lens having an optical axis and configured to focus the scanned beam of light to a point on the object to be imaged.

4. The laser digitizer of claim 3 where the image capture instrument comprises:
an image sensor configured to detect a triangulation image of the object, the triangulation image based on the pattern, wherein the pattern comprises a plurality of curves generated by scanning the beam of light on the object during an exposure period; and
a telecentric lens configured to focus the plurality of curves on the image sensor.

5. The laser digitizer of claim 4 further comprising an object positioning system configured to position the object within a field of projection of the scanner.

6. The laser digitizer of claim 5 where the object positioning system is configured to move the object to various positions and angles with respect to a field of view of the image capture instrument and the scanner.

7. The laser digitizer of claim 6 where the processor is programmed to merge multiple images of the object to create a three-dimensional map of the object.

8. The laser digitizer of claim 1 where the object comprises any one of: a dental model, a dental mold, or a dental casting.

9. The laser digitizer of claim 1 where the scanner comprises first and second mirrors, wherein the first and second mirrors are positioned substantially orthogonally with respect to one another.

10. The laser digitizer of claim 1 where the scanner comprises a rotatable mirror and a spinning polygon mirror.

11. The laser digitizer of claim 1 where the scanner further comprises a programmable position controller configured to control the scan of the collimated laser beam to a programmed scan sequence.

12. The laser digitizer of claim 1 wherein each of the set of curvilinear segments is substantially parallel to one another.

13. A method that generates a representation of a physical object comprising:
generating a multi-axis collimated beam of light;
with the physical object in a first position relative to the multi-axis collimated beam of light and during a first exposure period, scanning the multi-axis collimated beam of light towards the physical object, and detecting a reflection of the scanned collimated multi-axis beam of light from the physical object at a given triangulation angle, wherein over the first exposure period the scanned multi-axis collimated beam of light generates a first pattern comprising a plurality of segments and the reflection comprises a modified first pattern;
with the physical object in a second position relative to the multi-axis collimated beam of light and during a second exposure period, scanning the multi-axis collimated beam of light towards the physical object, and detecting a reflection of the scanned collimated multi-axis beam of light from the physical object at a given triangulation angle, wherein over the second exposure period the scanned multi-axis collimated beam of light generates a second pattern comprising a plurality of segments and the reflection comprises a modified second pattern; and
generating the representation of the physical object from data associated with the first and second modified patterns.

14. The method of claim 13 wherein the representation is a given surface characteristic of the physical object.

15. The method of claim 13 wherein the physical object is one of: a dental item, a dental impression, a dental model, a dental mold and a dental casting.

16. The method of claim 13 wherein each of the plurality of segments in at least one of the first and second patterns is a curve.

17. A laser digitizer, comprising:
a structure in which an object to be imaged is supported;
a light source having collimating optics configured to generate a collimated beam of light;
a scanner optically coupled to the light source and configured to scan the collimated beam along at least two axes towards the object to be imaged, wherein over a given exposure period the scanned collimated beam of light generates a pattern comprising a plurality of segments, wherein the structure is positionable relative to the scanned collimated beam so that, during first and second exposure periods, first and second patterns are projected onto first and second portions of the object;
an image capture instrument configured to detect a reflection of the scanned collimated beam from the object at a given triangulation angle θ, wherein over the first exposure period the reflection comprises a modified first pattern and over the second exposure period the reflection comprises a modified second pattern; and
a processor, under program control, that uses data associated with the modified first and second patterns to generate a representation of the object.

18. The laser digitizer as described in claim 17 wherein each segment is a curve.

* * * * *